United States Patent
Tabor

(10) Patent No.: US 9,545,306 B2
(45) Date of Patent: Jan. 17, 2017

(54) PROSTHETIC VALVE WITH SEALING MEMBERS AND METHODS OF USE THEREOF

(75) Inventor: Charles Tabor, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 528 days.

(21) Appl. No.: 13/091,765

(22) Filed: Apr. 21, 2011

(65) Prior Publication Data
US 2011/0264206 A1 Oct. 27, 2011

Related U.S. Application Data

(60) Provisional application No. 61/326,395, filed on Apr. 21, 2010.

(51) Int. Cl.
*A61F 2/24* (2006.01)
*A61F 2/82* (2013.01)
(Continued)

(52) U.S. Cl.
CPC ............... *A61F 2/2409* (2013.01); *A61F 2/24* (2013.01); *A61F 2/07* (2013.01); *A61F 2/2412* (2013.01);
(Continued)

(58) Field of Classification Search
CPC ............... A61F 2/07; A61F 2/90; A61F 2/06; A61F 2/24; A61F 2/2418; A61F 2250/0069; A61F 2/2412; A61F 2/2409; A61F 2230/0054; A61F 2220/0075; A61F 2/2436; A61F 2220/0016; A61F 2220/005; A61F 2250/006; A61F 2/2433; A61F 2230/005; A61F 2220/0008; A61F 2230/0078; A61F 2250/0039; A61F 2230/008; A61F 2/2439; A61F 2230/0065; A61F 2250/0003; A61F 2230/0067; A61F 2/2415; A61F 2210/0061; A61F 2230/0013; A61F 2/2445; A61F 2/246; A61F 2230/0069; A61F 2/013; A61F 2/2403; A61F 2002/9528; A61F 2210/0014; A61F 2220/0083; A61F 2230/0006; A61F 2250/001; A61F 2250/036; A61F 2/2442; A61F 2/82; A61F 2002/077; A61F 2220/0025; A61F 2220/0033; A61F 2220/0091; A61F 2250/0063; A61F 2250/0071; A61F 2/01; A61F 2/2457; A61F 2/2466; A61F 2/2487; A61F 2002/018; A61F 2002/075; A61F 2002/30545; A61F 2002/823; A61F 2002/8486; A61F 2002/9505; A61F 2002/9511
(Continued)

(56) References Cited

U.S. PATENT DOCUMENTS 3,657,744 A 4/1972 Ersek
3,671,979 A 6/1972 Moulopoulos
(Continued)

FOREIGN PATENT DOCUMENTS

EP 2047824 4/2009
EP 2193762 6/2010
(Continued)

*Primary Examiner* — Christian Sevilla
*Assistant Examiner* — Seema Mathew

(57) ABSTRACT

Embodiments of the present invention provide prosthetic valves having sealing members on the external surface thereof. The prosthetic heart valves of the present invention are preferably delivered by catheter directly through the apex of the heart or by other close range transcatheter delivery methods. Because these methods of implantation require a shorter length of catheter, a prosthetic valve can be
(Continued)

more accurately oriented in the desired implantation location. Fluoroscopy can be used to further assist in orientation of the valve. The sealing members of the present invention can be positioned on the prosthetic valve such that, when the prosthetic valve is implanted in a native annulus, each provided sealing member is located adjacent to a commissural point of the native valve leaflets. Because the sealing members are precisely oriented on the prosthetic valve, a physician can ensure that the sealing members are aligned with the commissural points of the native valve leaflets. In embodiments of the present invention, the prosthetic valve can have a waisted middle section, and the sealing members can be located in the waisted middle section such that the crimped diameter of the prosthetic valve is not negatively impacted by the sealing members.

11 Claims, 7 Drawing Sheets

(51) Int. Cl.
  *A61F 2/07* (2013.01)
  *A61F 2/962* (2013.01)
  *A61F 2/86* (2013.01)
(52) U.S. Cl.
  CPC .......... *A61F 2/2418* (2013.01); *A61F 2/2436* (2013.01); *A61F 2/82* (2013.01); *A61F 2/86* (2013.01); *A61F 2/962* (2013.01); *A61F 2220/0075* (2013.01); *A61F 2250/0069* (2013.01)
(58) Field of Classification Search
  USPC ............ 623/1.24, 2.11, 2.18, 1.26, 1.3, 1.32, 2.1, 623/2.17, 2.12
  See application file for complete search history.

(56) References Cited

U.S. PATENT DOCUMENTS

| | | | |
|---|---|---|---|
| 4,056,854 A | 11/1977 | Boretos et al. | |
| 5,370,685 A | 12/1994 | Stevens | |
| 5,545,214 A | 8/1996 | Stevens | |
| 5,814,097 A | 9/1998 | Sterman et al. | |
| 9,072,604 B1* | 7/2015 | Melnick | A61F 2/2418 |
| 9,132,007 B2* | 9/2015 | Menk | A61F 2/2418 |
| 9,314,335 B2* | 4/2016 | Konno | A61F 2/2412 |
| 9,433,500 B2* | 9/2016 | Chau | A61F 2/2412 |
| 2004/0186563 A1 | 9/2004 | Lobbi | |
| 2005/0137686 A1* | 6/2005 | Salahieh et al. | 623/2.11 |
| 2005/0137687 A1* | 6/2005 | Salahieh | A61F 2/2418 623/2.11 |
| 2005/0137695 A1 | 6/2005 | Salahieh et al. | |
| 2006/0004442 A1 | 1/2006 | Spenser et al. | |
| 2006/0259136 A1* | 11/2006 | Nguyen et al. | 623/2.18 |
| 2006/0271172 A1* | 11/2006 | Tehrani | A61F 2/2409 623/2.11 |
| 2007/0142907 A1* | 6/2007 | Moaddeb | A61F 2/2445 623/2.11 |
| 2007/0213813 A1* | 9/2007 | Von Segesser | A61F 2/2418 623/2.18 |
| 2008/0082164 A1* | 4/2008 | Friedman | A61F 2/2409 623/2.11 |
| 2008/1480189 | 6/2008 | Nguyen et al. | |
| 2008/0195199 A1* | 8/2008 | Kheradvar | A61F 2/2418 623/2.11 |
| 2009/0099653 A1* | 4/2009 | Suri et al. | 623/2.11 |
| 2009/0112311 A1* | 4/2009 | Miles | A61F 2/24 623/2.38 |
| 2010/0049306 A1* | 2/2010 | House et al. | 623/1.26 |
| 2010/0161036 A1* | 6/2010 | Pintor | A61F 2/2418 623/1.26 |
| 2010/0256723 A1* | 10/2010 | Murray | A61F 2/2418 623/1.2 |
| 2011/0319989 A1* | 12/2011 | Lane | A61F 2/2418 623/2.11 |
| 2012/0078360 A1* | 3/2012 | Rafiee | A61F 2/2418 623/2.37 |
| 2013/0317603 A1* | 11/2013 | McLean | A61F 2/2436 623/2.12 |
| 2014/0194975 A1* | 7/2014 | Quill | A61F 2/2427 623/2.11 |
| 2014/0209238 A1* | 7/2014 | Bonyuet | A61F 2/2415 156/294 |
| 2014/0222142 A1* | 8/2014 | Kovalsky | A61F 2/2418 623/2.17 |
| 2014/0222144 A1* | 8/2014 | Eberhardt | A61F 2/2418 623/2.38 |
| 2014/0243966 A1* | 8/2014 | Garde | A61F 2/2409 623/2.18 |
| 2014/0257475 A1* | 9/2014 | Gross | A61F 2/2439 623/2.38 |
| 2014/0277390 A1* | 9/2014 | Ratz | A61F 2/2418 623/1.26 |
| 2014/0277422 A1* | 9/2014 | Ratz | A61F 2/2418 623/2.37 |
| 2014/0277424 A1* | 9/2014 | Oslund | A61F 2/2418 623/2.38 |
| 2014/0303719 A1* | 10/2014 | Cox | A61F 2/2418 623/2.11 |
| 2014/0330371 A1* | 11/2014 | Gloss | A61F 2/2418 623/2.17 |
| 2015/0005863 A1* | 1/2015 | Para | A61F 2/2418 623/1.2 |
| 2015/0127098 A1* | 5/2015 | Braido | A61F 2/2418 623/2.17 |
| 2015/0142104 A1* | 5/2015 | Braido | A61F 2/2418 623/2.18 |
| 2015/0157455 A1* | 6/2015 | Hoang | A61F 2/2418 623/2.18 |
| 2015/0305860 A1* | 10/2015 | Wang | A61L 27/20 623/2.17 |
| 2015/0313711 A1* | 11/2015 | Chang | A61F 2/2427 623/2.11 |
| 2015/0351903 A1* | 12/2015 | Morriss | A61F 2/2418 623/2.11 |
| 2016/0030165 A1* | 2/2016 | Mitra | A61F 2/2409 623/2.42 |
| 2016/0030169 A1* | 2/2016 | Shahriari | A61F 2/2409 623/2.18 |
| 2016/0045316 A1* | 2/2016 | Braido | A61B 5/6862 623/2.38 |
| 2016/0143732 A1* | 5/2016 | Glimsdale | A61F 2/2418 623/2.41 |
| 2016/0151153 A1* | 6/2016 | Sandstrom | A61F 2/2418 623/2.18 |

FOREIGN PATENT DOCUMENTS

| | | | |
|---|---|---|---|
| FR | 99 14462 | 11/1999 | |
| WO | 93/01768 | 2/1993 | |
| WO | 97/28807 | 8/1997 | |
| WO | WO 2009042196 A2 * | 4/2009 | ............... A61F 2/24 |

* cited by examiner

PROSTHETIC VALVE WITH SEALING MEMBERS AND METHODS OF USE THEREOF

CROSS-REFERENCE TO RELATED APPLICATION

This application claims benefit under 35 U.S.C. 119(e) to U.S. Provisional Patent Application 61/326,395, filed Apr. 21, 2010, which is incorporated by reference herein in its entirety.

BACKGROUND OF THE INVENTION

Field of the Invention

The present invention relates to prosthetic heart valve assemblies and methods of preventing paravalvular leakage. More specifically, the present invention relates to the use of sealing members to seal gaps that can form between a valve frame and the wall of a native annulus when a prosthetic heart valve is implanted in the native annulus.

Background

Minimally invasive approaches have been developed to facilitate catheter-based implantation of valve prostheses on the beating heart, intending to obviate the need for the use of classical sternotomy and cardiopulmonary bypass. For example, International Application (PCT) Nos. WO 93/01768 and WO 97/28807, as well as U.S. Pat. No. 5,814,097 to Sterman et al., U.S. Pat. No. 5,370,685 to Stevens, and U.S. Pat. No. 5,545,214 to Stevens illustrate techniques for transcatheter implantation of stents and prosthetic valves that are not very invasive, as well as instruments for implementation of these techniques.

Although transcatheter delivery methods have provided safer and less invasive methods for replacing a defective native heart valve, leakage between the implanted prosthetic valve and the surrounding blood vessel is a recurring problem. Leakage can be particularly prevalent at the location of the commissural points of the native valve leaflets. At these commissural points, a gap can exist between the prosthetic valve frame and the wall of the native annulus. Attempts have been made to provide structures on the prosthetic valve to prevent leakage.

For example, U.S. Patent Publication No. 2007/0293944 to Spenser et al. ("Spenser") discloses methods of percutaneously repairing paravalvular leaks, including repair techniques and built-in leak prevention means. In one embodiment, a prosthetic valve is provided with flexible, self-expanding elements connected to the outer surface of the prosthetic valve. The self-expanding elements are positioned at even intervals around the surface of the prosthetic valve. A self-expanding element will expand if there is a gap between the implanted valve and the body lumen at the location of the self-expanding element, but will remain collapsed at the locations where the valve more closely abuts the body channel.

One disadvantage of this device arises because the prosthetic valve is designed for percutaneous implantation. Percutaneous transcatheter implantation requires a longer catheter than more direct transcatheter implantation methods such as delivery directly through the thoracic aorta or the apex of the heart. The longer catheter length limits the physician's ability to control the orientation of a prosthetic valve on the catheter. Because of this lack of control, it is difficult to align sealing elements directly with known inconsistencies of a native annulus, such as the gap that typically appears between the prosthetic valve and the wall of the native annulus at the commissural points of the native valve leaflets. Providing sealing elements at standard intervals along the circumference of the prosthetic valve does not guarantee that a particular gap between the prosthetic valve and the native annulus wall is filled with a sealing element. The valve may ultimately be positioned such that one of the empty spaces between two sealing elements is aligned partially or completely with a gap, thereby failing to prevent leakage through the gap.

Thus, there is a need for a prosthetic heart valve that can more accurately and predictably seal paravalvular leakage points by providing targeted commissural seal.

BRIEF SUMMARY OF THE INVENTION

Embodiments of the present invention provide prosthetic valves having sealing members on the external surface thereof. The prosthetic heart valves of the present invention are preferably delivered by catheter directly through the apex of the heart or by other close range transcatheter delivery methods. Because these methods of implantation require a shorter length of catheter, a prosthetic valve can be accurately oriented in the desired implantation location. Fluoroscopy can be used to further assist in orientation of the valve. The sealing members of the present invention can be positioned on the prosthetic valve such that, when the prosthetic valve is implanted in a native annulus, each provided sealing member is located adjacent to a commissural point of the native valve leaflets. Because the sealing members are precisely oriented on the prosthetic valve, a physician can ensure that the sealing members are aligned with the commissural points of the native valve leaflets. In embodiments of the present invention, the prosthetic valve can have a waisted middle section, and the sealing members can be located in the waisted middle section such that the crimped diameter of the prosthetic valve is not negatively impacted by the sealing members.

BRIEF DESCRIPTION OF THE FIGURES

The accompanying figures, which are incorporated herein, form part of the specification and illustrate embodiments of prosthetic valves with sealing members to prevent paravalvular leakage. Together with the description, the figures further serve to explain the principles of and to enable a person skilled in the relevant art(s) to make and use the prosthetic valves and sealing members described herein. In the drawings, like reference numbers indicate identical or functionally similar elements.

DETAILED DESCRIPTION OF THE INVENTION

The following detailed description of prosthetic heart valves with sealing members and methods to seal paravalvular leakage refers to the accompanying figures that illustrate exemplary embodiments. Other embodiments are possible. Modifications can be made to the embodiments described herein without departing from the spirit and scope of the present invention. Therefore, the following detailed description is not meant to be limiting. Further, it would be apparent to one of skill in the art that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

Figure 1:
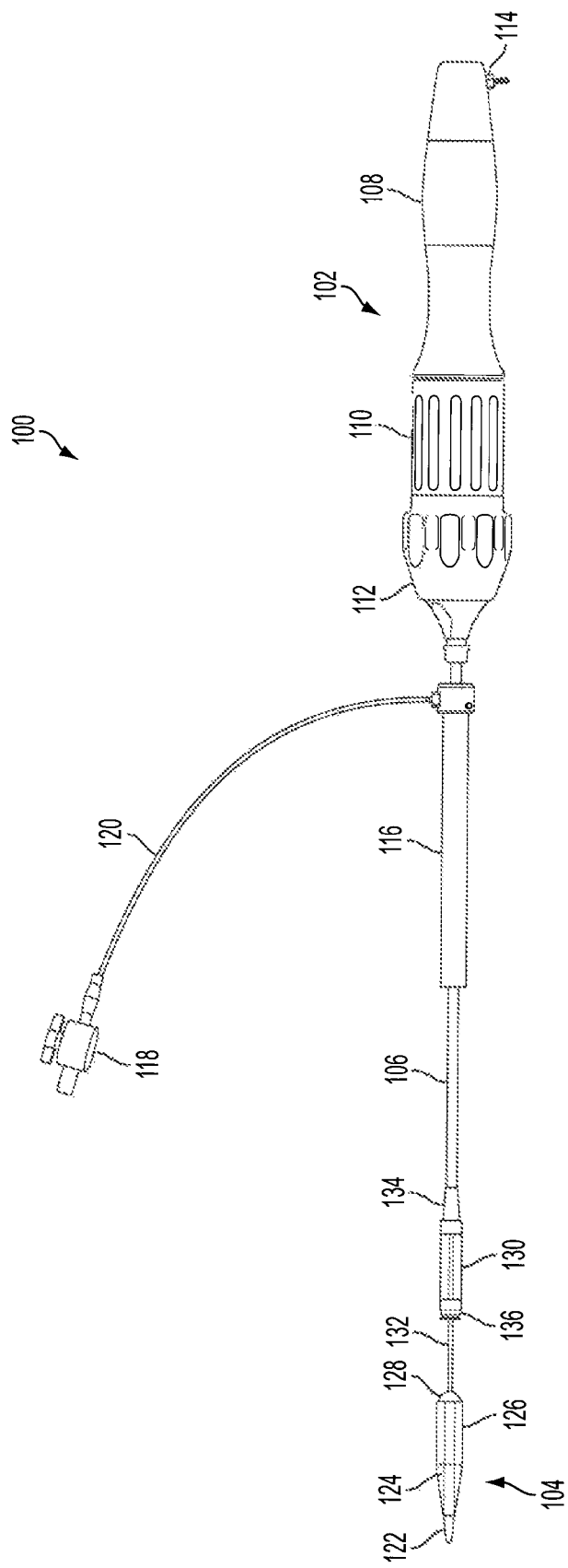
FIG. 1 illustrates a catheter assembly in accordance with one embodiment presented herein.

FIG. 1 illustrates a catheter assembly 100 in accordance with one embodiment presented herein. Catheter assembly 100 generally includes a handle assembly 102 located at the proximal end of the catheter, a distal tip assembly 104 located at the distal end of the catheter, and an introducer 116 slidably located along an outer delivery shaft 106 between the distal tip assembly 104 and the handle assembly 102.

Outer delivery shaft 106 is preferably a tubular flexible braided structure. Outer delivery shaft 106 can be formed of braided material fabricated from materials such as, but not limited to, polyethylene naphthalate (PEN), polyester (PET), stainless steel, titanium, nitinol, cobalt nickel alloy, polyamide, polyimide, or the like. In some embodiments, outer delivery shaft can contain reinforcing materials or structures. These structures can include an inner polymer layer overlaid by a first reinforcing braid layer, overlaid by a coil reinforcement, finally overlaid with an outside layer of polymeric material. In another embodiment, the inner layer of polymeric material is overlaid by the coil reinforcement, which is overlaid by the braided reinforcement, which is finally overlaid with the outside layer of a polymeric material. In other embodiments, the inner layer of polymeric material is overlaid by a braided layer, which is overlaid by the coil winding, which is overlaid by another layer of braid, which is in turn overlaid by an outer polymeric layer. Preferably, however, any reinforcing layer used allows outer delivery shaft 106 to retain a degree of flexibility. Other flexible materials can also be used to form outer delivery shaft 106 consistent with embodiments of the present invention.

Handle assembly 102 includes a main handle 108, a proximal control knob 110, and a distal control knob 112. Main handle 108, a proximal control knob 110, and distal control knob 112 can be formed of any suitable material. For example, in some embodiments the handle and control knobs are formed of a polymer material. Other materials are possible, as would be understood in the art. A flushing port 114 can also be included on main handle 108. Flushing port 114 can be used to de-air the catheter assembly. Also, the native annulus is exposed to the blood pressure in a patient's cardiovascular system during use of a heart valve delivery catheter. As a consequence, in the absence of any counter pressure in the annulus, blood can flow inside towards the proximal end of the catheter, where it can coagulate and cause thrombosis. Thus, flushing port 114 can also allow fluid to be introduced into the native annulus to prevent such complications. In some embodiments, flush port 114 can also be used for site specific drug delivery or to introduce radiopaque fluid into the body.

As will be described herein, proximal control knob 110, and distal control knob 112 can be manipulated by a user in order to control operation of the distal tip assembly 104 of catheters described herein. Distal tip assembly 104 includes a tip 122, which is preferably slotted for the reasons described herein, a tip connector 124, and a support arm sleeve 126. A flushing tap 118 and a flushing tap lead 120 can be connected to an introducer 116. Introducer 116 is preferably a tubular member that is slidably located over outer delivery shaft 106. Introducer 116 may be formed of a variety of materials, for example, stainless steel or various polymer materials. A catheter is configured to be advanced along a guide wire (not shown). Preferably, the catheter is advanced over a 0.035 inch guide wire. However, the dimensions of the catheter components can be adjusted for advancement over guide wires with larger or smaller diameters.

Catheter assembly 100 further includes a valve retaining sleeve 130, a valve retaining sleeve connector 134, a valve retainer 136, and a tip guard 128, Valve retaining sleeve connector 134 secures valve retaining sleeve 130 to the distal end of the outer delivery shaft 106. The outer delivery shaft 106 therefore extends from the interior of handle assembly 102 to sleeve connector 134. Slotted tip 122 and tip guard 128 are positioned on and connected to the distal end of an intermediate delivery shaft 132. Intermediate delivery shaft 132 extends from the interior of handle assembly 102 to slotted tip 122, to which the distal end of intermediate delivery shaft 132 is attached. Intermediate delivery shaft 132 is encompassed by outer delivery shaft 106 from the interior of handle assembly 102 until the outer delivery shaft 106 ends at sleeve connector 134. Tip guard 128 is attached to the proximal end of slotted tip 122. In one embodiment, tip guard 128 can be attached directly to intermediate shaft 132. Intermediate shaft 132 is preferably a tubular member.

It is understood that handle assembly 102 is merely an exemplary embodiment of a catheter handle that can be used to deliver the prosthetic valves having sealing members described herein. The present invention is not limited to catheters having handles such as those described herein. The prosthetic valves having sealing members and methods of preventing paravalvular leakage described herein can be used with catheters having different types of handles, including, e.g., conventional hand controlled catheter handles. It is further understood that the sealing members described herein can be used in conjunction with prosthetic valves other than those described herein.

A guide wire shaft is encompassed within intermediate shaft 132 and extends from the inside of handle assembly 102 to the proximal end of slotted tip 122. Thus, in one embodiment of the present invention, at least three shafts extend from the main handle, and the shafts are nested along at least a part of their lengths. Specifically, a guide wire shaft (not shown) is encompassed by the intermediate delivery shaft 132 from a position inside of handle assembly 102 to the interior of slotted tip 122, which is preferably hollow through at least a portion thereof. Intermediate delivery shaft 132 is connected to, and ends, at the proximal end of slotted tip 122. In turn, intermediate delivery shaft 132 is encompassed by the outer delivery shaft 106 from a position inside of handle assembly 102 to the valve retaining sleeve connector 134. In at least certain embodiments, outer delivery shaft 106 is connected to, and ends, at the retaining sleeve connector 134. In at least certain embodiments, intermediate shaft 132 and the guide wire shaft (not shown) can be constructed of various polymer materials, and may be braided structures using materials described above with reference to outer delivery shaft 106.

Figure 2:
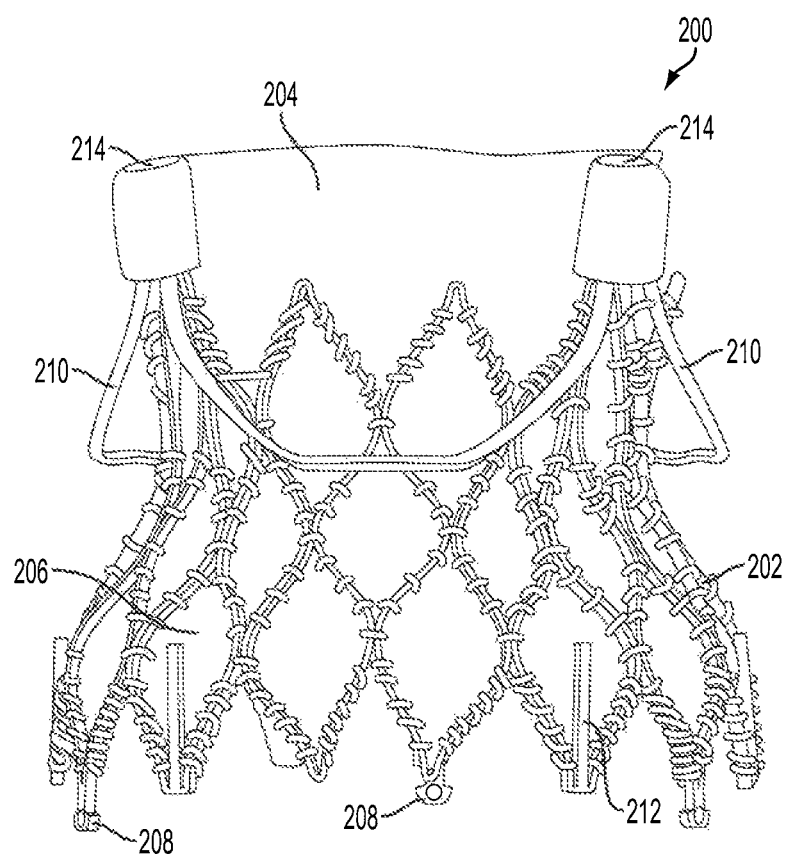
FIG. 2 is a depiction of one of the many types of prosthetic valves that can be used in conjunction with the sealing members described herein.

FIG. 2 depicts an exemplary prosthetic heart valve 200. Prosthetic heart valve 200 is illustrated herein in order to facilitate description of the methods and devices to prevent paravalvular leakage according to embodiments of the present invention. It is understood that any number of alternate prosthetic heart valves can be used with the methods and devices described herein. Prosthetic heart valve 200 is merely exemplary. Prosthetic heart valve 200 includes support frame 202, valve leaflets 204 located towards the distal end of support frame 202, valve skirt 206, and three fixation hooks 208 extending from the proximal end of support frame 202. Commissural posts 214 are provided in the distal end of support frame 202. Support frame 202 is preferably formed of a self-expanding material, e.g., nitinol. Other self-expanding or shape memory materials can be used instead of nitinol. Preferably, three valve leaflets 204 are provided to form a tricuspid valve structure within prosthetic heart valve 200. It is understood that alternate valve leaflet configurations, e.g., bicuspid valves, can be included in prosthetic heart valves for use in conjunction with the crimping devices and methods described herein. Leaflets 204 and skirt 206 are preferably formed of animal pericardium tissue, such as, e.g., bovine pericardium or porcine pericardium. In other embodiments, leaflets 204 and skirt 206 can be formed from synthetic materials. Leaflets 204 and skirt 206 are attached to support frame 202, preferably using sutures, as shown in FIG. 2. Various types of sutureless bonding methods can be used to attach leaflets 204 and skirt 206 to frame 202.

Fixation hooks 208 extend from the proximal inflow end of support frame 202 and include eyelets at their proximal end. Fixation hooks 208, which are optional, can be formed in various configurations other than that shown. For example, fixation hooks 208 can be J shaped hooks or eyelets 208 can take on any number of sizes or shapes while remaining compatible with the crimping devices and methods described herein.

Support frame 202 further includes three support arms 210, which are attached to support frame 202 towards its distal outflow end. Alternately, support arms 210 can be formed integrally with support frame 202. Support arms 210 are preferably formed of a self-expanding material, e.g., nitinol. Other self-expanding or shape memory materials can be used instead of nitinol. Support arms 210 can be attached to support frame 202 such that they are biased away from support frame 202 but can pivot radially with respect to support frame 202. When the prosthetic heart valve 200 is implanted in the native annulus of a patient, support arms 210 rest on the body tissue in the root of the aorta adjacent to the outflow end of the native annulus, thereby bracing the prosthetic heart valve 200.

A plurality of barbs 212 can be provided on the proximal end of support frame 202. Barbs 212 extend for a distance towards the distal end of support frame 202. Preferably, barbs 212 extend in an approximately axial direction. Barbs 212, which are optional, can also be biased or curved slightly inward, but with less inward curve than the surrounding section of support frame 202. Because the distal end of barbs 212 define a greater diameter than the surrounding support frame, they receive the majority of forces when the proximal end of support frame 202 is crimped. This prevents damage to support frame 202 and, more particularly, to the sutures attached skirt 206 to support frame 202.

Figure 3:
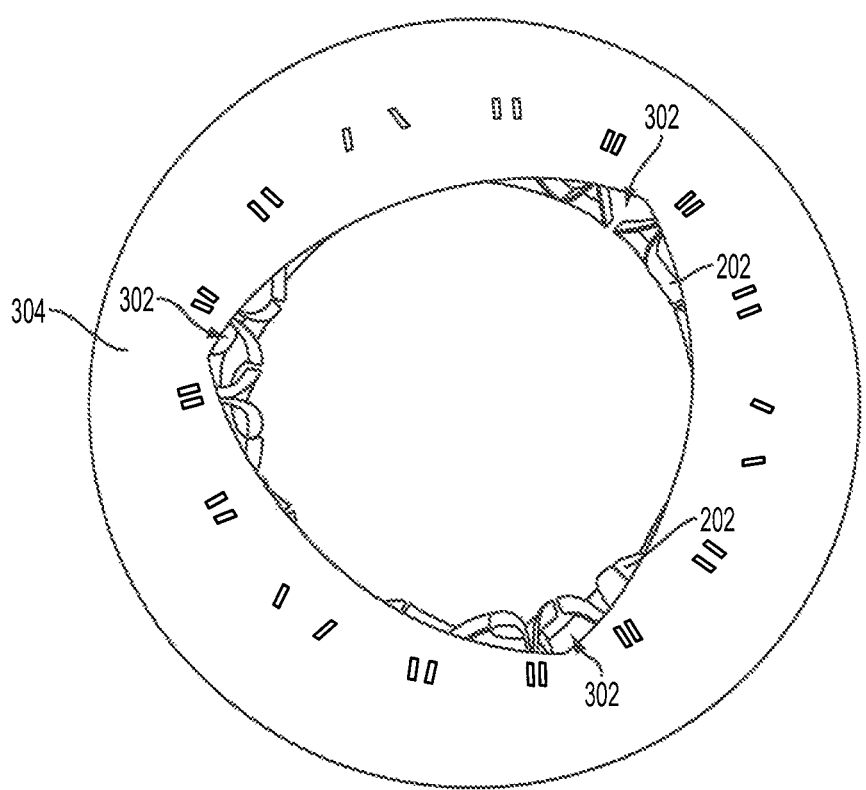
FIG. 3 is a top-down view of a native annulus with a prosthetic valve implanted therein.

FIG. 3 is a top-down view of a native annulus 304 with the support frame 202 of prosthetic heart valve 200 implanted therein. As can be seen in FIG. 3, native annuli are not perfectly rounded. Particularly, a native annulus 304 often can have indentations corresponding to the commissural points of the native valve leaflets. As a result, prosthetic heart valves having an approximately circular shape do not provide an exact fit in a native annulus. Gaps 302 can therefore exist between support frame 202 and native annulus 304, particularly at the location of commissural posts 214. As the prosthetic valve assumes responsibility for regulating blood flow through the native annulus, gaps 302 can result in leakage. This leakage is referred to in the art as a valvular or paravalvular leak. Embodiments of the present invention include sealing members that can occlude gaps 302, thereby reducing, minimizing, or eliminating leaks therethrough.

Figure 4:
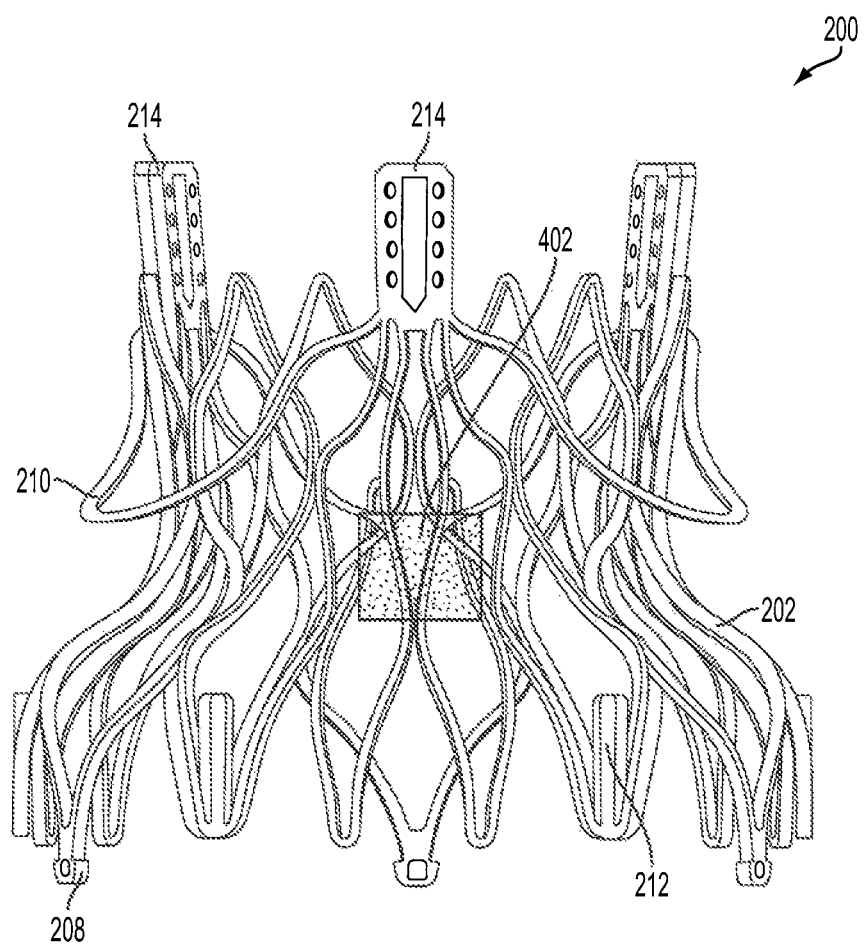
FIG. 4 depicts the prosthetic valve of FIG. 2 with sealing members mounted thereon.

FIG. 4 depicts the prosthetic valve of FIG. 2 with sealing members 402 mounted thereon. For the sake of simplicity of illustration, valve material 204 is not depicted in FIG. 4. Sealing members 402 can be mounted on the prosthetic heart valve 200 by a variety of methods. For example, sealing members 402 can be sutured to frame 202 or to skirt 206. Sealing members 402 can be positioned roughly in line with commissure posts 214. Sealing members 402 can also be mounted to prosthetic heart valve 200 by gluing, or by other methods known in the art.

Although depicted in FIG. 4 in abstract form only, sealing members can be formed of a variety of materials consistent with the functional requirements of the sealing members. Sealing members 402 can be formed of a polyethylene terephthalate material, such as Dacron. Sealing members 402 can also be formed of biological or artificial tissue, or other similar materials. Sealing members 402 can be pads. Although not illustrated, each sealing member can include multiple pads or sub-members. The pads or sub-members can be aligned horizontally or longitudinally on the prosthetic valve 200, or can be unaligned. Preferably, sealing members 402 are positioned on a prosthetic valve such that, when the prosthetic valve is implanted in a native annulus, the sealing members 402 are aligned with the commissural points of the native valve leaflets.

The sealing members 402 can be formed of polyethylene terephthalate material surrounding other materials in order to add size or density to the sealing members 402. For example, a hydrophilic sponge or double velour fabric could be wrapped in a polyethylene terephthalate material in order to form sealing members 402. Sealing members 402 can also be formed of multiple layers of a polyethylene terephthalate material or biological tissue. In addition, a self-expanding frame, for example, a nitinol frame, can be provided with a tissue or polyethylene terephthalate covering in order to further reduce the profile of sealing members 402 during delivery to a desired position in a patient's body. However, if the sealing members 402 are located at the waisted crimpdown region of valve frame 202, it is not required to utilize sealing members 402 that can be reduced in size for delivery and then expanded in the body because of the radial space created by the waisted crimpdown region, as explained in further detail with reference to FIG. 6. Similarly, non-expandable sealing members 402 can be provided at the bottom end of the valve frame 202.

Sealing members 402 can be formed in a variety of shapes and sizes consistent with embodiments of the present invention. Preferably, three independent sealing members 402 are provided, each sealing member 402 being longitudinally aligned with a commissural post 214. The sealing members 402 can be substantially evenly spaced around the prosthetic valve. In this configuration, sealing members 402 will be positioned in or directly adjacent to gaps 302 when the prosthetic heart valve 200 is positioned in a native annulus such that commissural posts 214 are aligned with the commissural points of the native valve leaflets. In other embodiments, sealing members 402 can additionally or alternatively be located at midway points between commissural posts 214 to prevent paravalvular leakage caused, for example, by excessive stenosis. Alternatively, sealing members can be placed at any suitable position on the prosthetic valve by the attending physician to account for generally known locations of paravalvular leakage. In most embodiments, sealing members 402 are located at each of the commissural posts 214, but in other embodiments, sealing members 402 can be located at other suitable locations on the heart valve. In a preferred embodiment, the prosthetic heart valve includes commissural posts, but in other embodiments, the prosthetic heart valve does not include commissural posts. In another embodiment, a continuous circumferential sealing member (not shown) can be used. The circumferential pad can extend around the circumference of the support frame 202 at the waisted middle region of the frame 202, or at other regions of the frame 202, such as near the inflow section or near the outflow section. The circumferential pad can have sections with varying densities and dimensions. For example, the density or size of the circumferential pad can be increased at the areas of the pad that are longitudinally aligned with commissural posts 214 in order to ensure that gaps 302 are occluded. The remainder of the circumferential pads can be of a lower density or a smaller size to occlude smaller irregularities in the native annulus that can form leakage gaps.

Sealing members 402 can be attached to the frame 202 by a variety of methods. For example, sealing members 402 can be attached to the frame 202 by suturing direction to the frame 202. In another embodiment, sealing members 402 can be secured to frame 202 by suturing to skirt 206. One skilled in the art would understand that other methods can be used to secure sealing members 402 to frame 202. Although only one sealing member is shown in FIG. 4, three seals pads 402 are preferably provided with prosthetic heart valve 200 in order to seals the three gaps 302 corresponding to the commissural points of the native aortic valve leaflets. Sealing members 402 are preferably aligned with commissural posts 214 of prosthetic valve frame 202. Preferably, prosthetic heart valve 200 is implanted in a native annulus 304 such that, after being expanded to its deployed configuration, the commissural posts 214 are oriented in the native annulus 304 in a position corresponding to the commissural points of the native valve leaflets.

Figure 5:
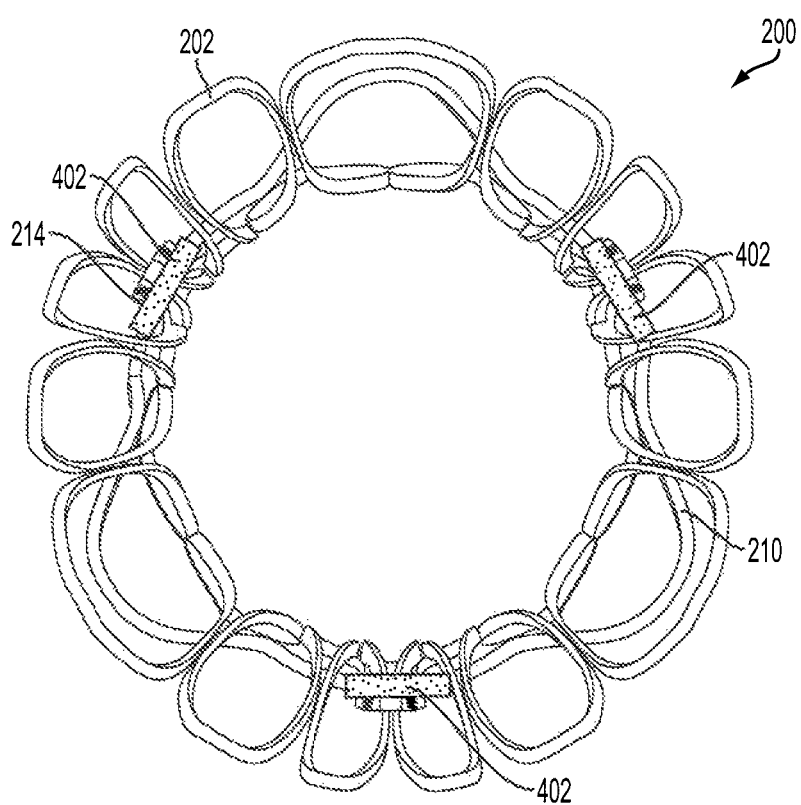
FIG. 5 is a top-down view of the prosthetic valve of FIG. 2.

FIG. 5 is a top-down view of a prosthetic valve according to one embodiment of the present invention in an expanded deployed configuration. As can be seen in FIG. 5, three sealing members 402 are secured to frame 202. The sealing members 402 are generally aligned longitudinally with the commissural posts 214 of the valve frame 202. It is understood that sealing members 402 can be located at other locations on valve frame 202 depending on the desired orientation of valve frame 202 in a native annulus. The size and shape of sealing members 402 in the figures presented herein is merely exemplary. A variety of shapes and sizes can be used. Preferably, sealing members 402 extend sufficiently radially from frame 402 to contact the wall of the native annulus at the position of gaps 302. In one embodiment, prosthetic heart valves having sealing members 402 of various sizes and shapes can be provided such that a physician can select a valve having sealing members that correspond in size to the expected size of gaps 302 in a particular patient. The prosthetic heart valves of the present invention are preferably delivered by catheter directly through the apex of the heart or by other close range transcatheter delivery methods. Because these methods of implantation require a shorter length of catheter, a prosthetic valve can be more accurately oriented in the desired implantation location. Fluoroscopy can be used to further assist in orientation of the valve.

Figure 6:
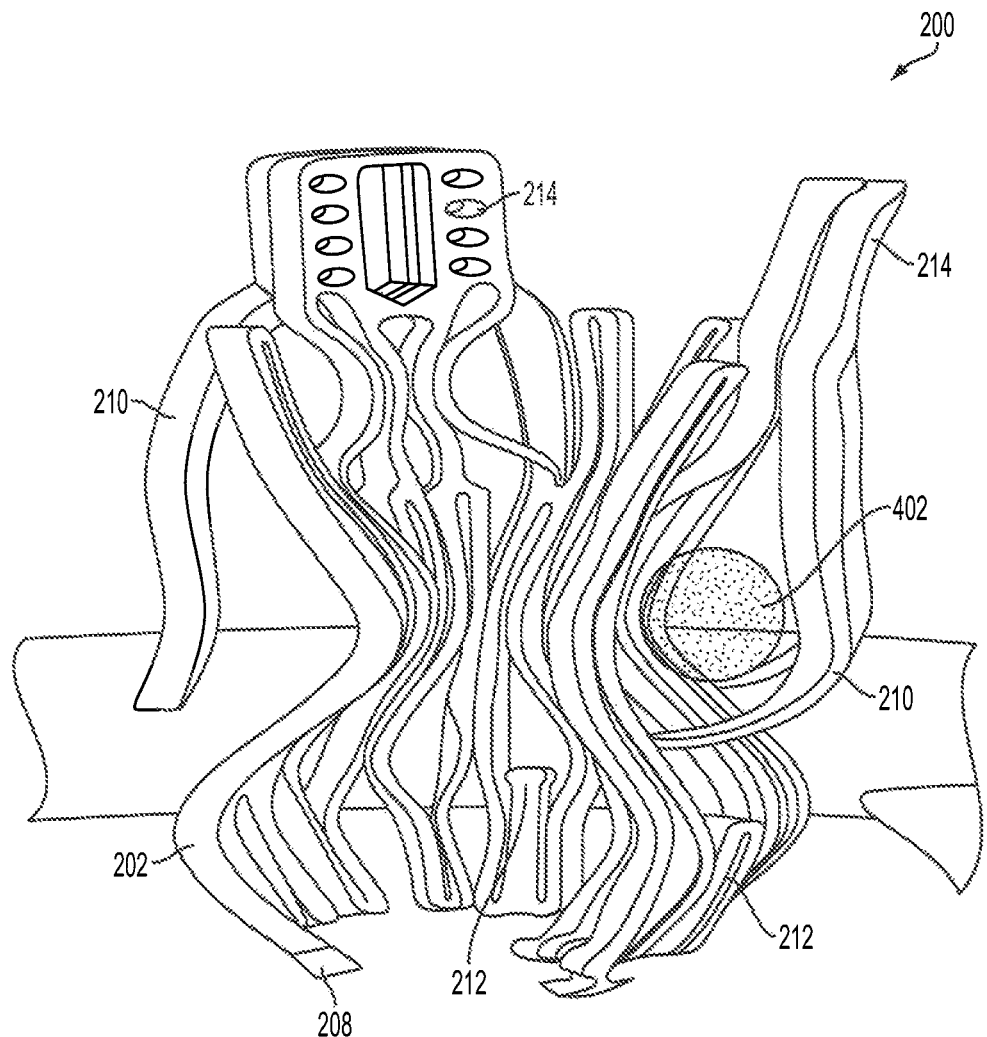
FIG. 6 is a cross-sectional side view of the prosthetic valve of FIG. 2 in a crimped configuration.

FIG. 6 is a cross-sectional side view of the prosthetic heart valve 200 of FIG. 2 in a crimped configuration for delivery to a desired location in a patient's body via catheter. After being delivered to a desired location in a patient's body, the prosthetic heart valve 200 can be removed from the catheter and allowed to return to its expanded shape. Prosthetic heart valve 200 can be expanded in situ by a balloon catheter. Prosthetic heart valve 200 can also be formed of a shape memory material, such as nitinol, such that prosthetic heart valve 200 will return to its expanded shape after the prosthetic heart valve 200 is forced out of a catheter.

As seen in FIG. 6, the middle portion of the valve frame 202 has a smaller diameter than the end portions of the valve frame 202 when the prosthetic heart valve 200 is in its crimped position. Due to this configuration, sealing members 402, which preferably are mounted to the middle portion of valve frame 202, do not increase the maximum diameter of the prosthetic heart valve 200 when the prosthetic heart valve 200 is in the crimped configuration. In use, an individual can load prosthetic heart valve 200 in catheter assembly 100 by radially contracting prosthetic valve 200 so that sealing members 402 do not extend beyond the maximum diameter of an outer surface of prosthetic valve 200, including support frame 202 and support arms 210. This configuration thereby reduces the possibility that sealing members 402 will be damaged by snagging on the catheter during loading.

Although sealing members 402 are shown in FIG. 6 as spheres or circular pads, sealing members 402 can be formed in a variety of shapes, for example, barrel, rectangular, square, cubical, or oblong shapes. Although only one sealing member 402 is illustrated in FIG. 6 due to the cross-sectional representation, it is understood that additional sealing members 402 can be provided with heart valve prosthesis 200. Preferably, three sealing members 402 are provided, and each sealing member 402 is aligned with one of the commissural posts 214. Sealing members 402 can be provided at other positions around the circumference of valve frame 202 if desired. Sealing members 402 can also be positioned at other positions along the length of heart valve prosthesis 200. For example, one or more sealing members 402 can be positioned below the waisted crimpdown region of valve frame 202 and below the valve leaflets 204. It is understood that if sealing, members 402 did increase the crimpdown diameter, for example, if larger sealing members 402 are used, or if sealing members 402 are located outside of the waisted middle region of valve frame 202, the prosthetic heart valve 200 could be delivered to patients that can accept a slightly larger diameter delivery system.

Figure 7:
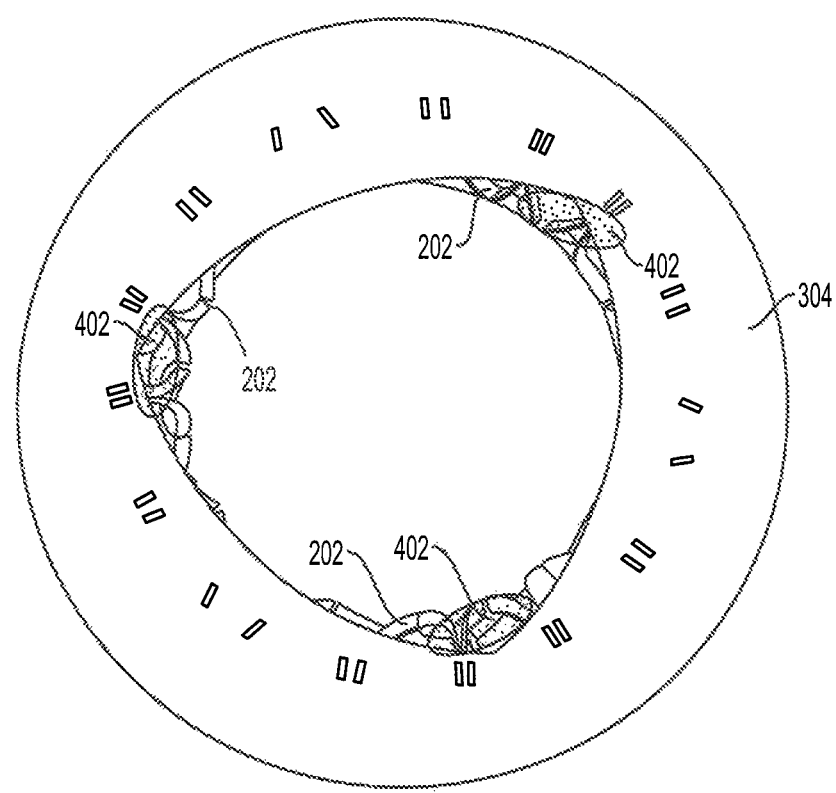
FIG. 7 is a top-down view of a native annulus with a prosthetic valve implanted therein. The valve depicted in FIG. 7 is equipped with sealing members.

FIG. 7 is a top-down view of a native annulus with a prosthetic valve implanted therein. The valve depicted in FIG. 7 is equipped with three sealing members 402 corresponding to the three gaps 302 between the valve frame 202 and the native annulus at the position of the commissural points of the native valve leaflets. Sealing members 402 prevent paravalvular leakage through gaps 302, resulting in more efficient operation of the prosthetic heart valve 200

The foregoing description of the invention has been presented for purposes of illustration and description. It is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

EXAMPLES

The following paragraphs serve as examples of the above-described embodiments.

Example 1

One embodiment of the present invention provides a prosthetic heart valve assembly comprising a prosthetic valve having a circumferential wall with an inner surface and an outer surface. The prosthetic valve is radially contractible and expandable for transcatheter delivery to a native annulus. Three sealing members are mounted on the prosthetic valve and substantially evenly placed around the prosthetic valve. The sealing members are configured to engage the commissure points of leaflets of a native valve to prevent paravalvular leakage.

The prosthetic valve can include an inflow section, an outflow section, and a waisted middle section having an expanded diameter less than the expanded diameters of the inflow section and the outflow section. The sealing members can be positioned in the waisted middle section of the prosthetic valve. The sealing members can include at least one pad. At least one of the sealing members can include two pads. The prosthetic valve can include support arms extending from the outer surface of the circumferential wall, and the support arms can be configured to contact tissue adjacent to an outflow end of a native annulus to brace the prosthetic valve in position. Sealing members can include polyethylene terephthalate. The sealing members can include biological tissue.

Example 2

Another embodiment provides a prosthetic heart valve assembly including a prosthetic valve with a circumferential wall having an inner surface and an outer surface. The prosthetic valve has an inflow section, an outflow section, and a waisted middle section with an expanded diameter less than the expanded diameters of the inflow section and the outflow section. At least one commissural seal pad is mounted on the prosthetic valve at a location corresponding to the commissural points of the leaflets of a native valve. The commissural seal pads are configured to prevent paravalvular leak. The at least one commissural seal pad is positioned in the waisted middle section of the prosthetic valve.

The commissural seal pad can be formed of polyethylene terephthalate or biological tissue. The prosthetic valve can include commissural posts for supporting tissue leaflets, and the at least one commissural seal pad can be mounted to the frame at a location that is longitudinally aligned with a commissural post. Three commissural seal pads can be mounted on the prosthetic valve. The at least one commissural seal pad can include a circumferential commissural seal pad extending around the circumference of the waisted middle section of the prosthetic valve. The size of the circumferential commissural seal pad can vary along the length of the circumferential commissural seal pad. The size of the circumferential commissural seal pad can be the largest at portions of the circumferential commissural seal pad that are longitudinally aligned with the commissural posts.

What is claimed is:

1. A prosthetic heart valve assembly comprising:
a prosthetic valve including a circumferential wall having an inner surface and an outer surface, wherein the prosthetic valve is radially contractible and expandable for transcatheter delivery to a native annulus; and
two or more sealing members mounted on the prosthetic valve and substantially evenly placed around the prosthetic valve, wherein the sealing members have a size and shape corresponding to gaps existing between the implanted prosthetic valve and the native valve and are configured to engage the gaps to prevent paravalvular leakage;
wherein the two or more sealing members protrude from the outer surface of the prosthetic valve in both a crimped configuration before the prosthetic valve is implanted and a deployed configuration after the prosthetic valve is implanted; and
wherein the two or more sealing members do not extend beyond a maximum diameter of the outer surface of the prosthetic valve when the prosthetic valve is in the crimped configuration before the prosthetic valve is implanted.

2. The prosthetic heart valve assembly of claim 1, wherein the prosthetic valve comprises an inflow section, an outflow section, and a waisted middle section having an expanded diameter less than the expanded diameters of the inflow section and the outflow section, and wherein the sealing members are positioned in the waisted middle section of the prosthetic valve.

3. The prosthetic heart valve assembly of claim 1, wherein the sealing members include at least three sealing members configured to engage three commissure points of leaflets of a native tricuspid valve to prevent paravalvular leakage.

4. The prosthetic heart valve assembly of claim 3, wherein the sealing members include three additional sealing members positioned approximately midway between the commissural points of a native tricuspid valve.

5. The prosthetic heart valve assembly of claim 1, wherein the sealing members comprise at least one pad.

6. The prosthetic heart valve assembly of claim 5, wherein at least one of the sealing members includes two pads.

7. The prosthetic heart valve assembly of claim 5, wherein the prosthetic valve comprises support arms extending from the outer surface of the circumferential wall, and the support arms are configured to contact tissue adjacent to an outflow end of a native annulus to brace the prosthetic valve in position.

8. The prosthetic heart valve assembly of claim 1, wherein the sealing members comprise polyethylene terephthalate.

9. The prosthetic heart valve assembly of claim 1, wherein the sealing members comprise biological tissue.

10. The prosthetic valve of claim 1 further comprising:
two or more commissural posts, wherein each of the at least two sealing members is longitudinally aligned with a corresponding one of the two or more commissural posts.

11. The prosthetic valve of claim 10, wherein each of the at least two sealing members have a size capable of occluding gaps created between the native annulus and the commissural posts.

* * * * *